(12) United States Patent
Roa-Espinosa

(10) Patent No.: US 9,051,538 B1
(45) Date of Patent: Jun. 9, 2015

(54) SEPARATION OF BIOCOMPONENTS FROM DDGS

(71) Applicant: Aicardo Roa-Espinosa, Madison, WI (US)

(72) Inventor: Aicardo Roa-Espinosa, Madison, WI (US)

(*) Notice: Subject to any disclaimer, the term of this patent is extended or adjusted under 35 U.S.C. 154(b) by 0 days.

(21) Appl. No.: 14/518,310

(22) Filed: Oct. 20, 2014

Related U.S. Application Data

(63) Continuation-in-part of application No. 14/190,332, filed on Feb. 26, 2014.

(51) Int. Cl.
| | |
|---|---|
| *C02F 1/24* | (2006.01) |
| *C02F 1/52* | (2006.01) |
| *C02F 1/54* | (2006.01) |
| *C02F 3/10* | (2006.01) |
| *C02F 9/00* | (2006.01) |
| *B03D 1/01* | (2006.01) |
| *B03D 1/02* | (2006.01) |
| *B03D 1/10* | (2006.01) |
| *B30B 13/00* | (2006.01) |
| *C11B 13/00* | (2006.01) |
| *C12F 3/10* | (2006.01) |
| *C07K 1/30* | (2006.01) |
| *C08B 1/00* | (2006.01) |
| *C02F 103/32* | (2006.01) |

(52) U.S. Cl.
CPC ... *C12F 3/10* (2013.01); *C02F 1/24* (2013.01); *C02F 1/5272* (2013.01); *C07K 1/30* (2013.01); *C11B 13/00* (2013.01); *C08B 1/00* (2013.01); *C02F 2103/32* (2013.01); *C02F 3/10* (2013.01); *B03D 1/01* (2013.01); *B03D 1/02* (2013.01); *B03D 1/10* (2013.01); *C02F 9/00* (2013.01); *B30B 13/00* (2013.01)

(58) Field of Classification Search
CPC .............. C02F 3/00; C02F 3/06; C02F 3/10; C02F 1/24; C02F 1/52; C02F 1/5272; C02F 1/40; C02F 9/00; C02F 2103/32; C02F 2103/322; C02F 2103/365; C02F 1/54; B01D 36/00; B01D 36/003; B01D 36/008; B01D 36/04; B01D 37/00; B01D 37/63; B01D 33/06; B01D 33/013; C11B 13/00; C08B 1/00; B03D 1/01; B03D 1/10; B30B 13/00; C12F 3/10; C07K 1/30
USPC ............ 100/35, 70 R, 71, 73–75, 90, 92, 94, 100/102, 37; 209/12.1, 13, 164, 166; 210/769, 704, 705, 726–728, 732–735, 210/770, 771, 774, 780, 784, 799, 806, 210/808; 241/20, 21, 24, 24.19, 24.21, 241/24.29; 435/71.1, 289.1, 297.1, 160, 435/161, 163, 165; 44/307, 605; 426/18, 426/49, 52, 417, 549, 622; 203/39, 42, 47
See application file for complete search history.

(56) References Cited

U.S. PATENT DOCUMENTS 7,014,774 B2 * 3/2006 Yamada et al. ............... 210/708
7,857,872 B2 * 12/2010 Krasutsky et al. ............. 44/605

(Continued)

*Primary Examiner* — Joseph Drodge
(74) *Attorney, Agent, or Firm* — Steven H. Greenfield; Greenfield Invention and Patent Consulting, Inc.

(57) ABSTRACT

A multi stage process for the separation of bio-components from a waste stream containing Dried Distillers Grains with Solubles is disclosed. Targeted polymers are added to the source and separated streams prior to passing the streams through separation equipment including a rotary screen, a press, and a dissolved air floatation in which the waste stream is separated into a stream containing predominantly protein, a stream containing predominantly oil, a stream containing predominantly water and a stream that contains predominantly fibers.

11 Claims, 2 Drawing Sheets

(56) References Cited

U.S. PATENT DOCUMENTS

| | | | |
|---|---|---|---|
| 2006/0006116 A1* | 1/2006 | Scheimann et al. | 210/728 |
| 2008/0026101 A1* | 1/2008 | Nickel et al. | 426/52 |
| 2010/0178675 A1* | 7/2010 | Lawton et al. | 435/71.1 |
| 2010/0224711 A1* | 9/2010 | Kreisler et al. | 241/21 |
| 2011/0079219 A1* | 4/2011 | McDonald et al. | 127/1 |
| 2012/0045545 A1* | 2/2012 | Mielgo et al. | 426/31 |
| 2012/0125859 A1* | 5/2012 | Collins et al. | 210/708 |
| 2013/0164795 A1* | 6/2013 | Lowe et al. | 435/134 |

* cited by examiner

SEPARATION OF BIOCOMPONENTS FROM DDGS

RELATED APPLICATIONS

This application is a continuation in part application claiming priority from non-provisional application Ser. No. 14/190,332 filed on Feb. 26, 2014.

FIELD OF THE INVENTION

The present invention relates generally to a process of recovering useful materials from waste sources that include Dried Distillers Grains with Solubles also known by the acronym DDGS, waste materials from ethanol production and animal feed waste.

BACKGROUND OF THE INVENTION

Thin stillage and distillers' grains are byproducts remaining after alcohol distillation from a fermented cereal grain mash. Both byproducts are used as energy and protein sources for ruminants. There are two main sources of these byproducts. The traditional sources were from brewers. However, more recently, ethanol plants such as corn, sugar cane, cassaya and potatoes have become a growing source.

DDGS contain valuable bio-materials mainly fibers, oil and protein. The oil in DDGS could be used either as cooking oil or as a biofuel. The main protein in corn is Zein which has been used in the manufacture of a wide variety of commercial products, including coatings for paper cups, soda bottle cap linings, clothing fabric, buttons, adhesives, coatings and binders, recently this protein has been used as a coating for candy, nuts, fruit, pills, and other encapsulated foods and drugs. Additionally Zein can be further processed into resins and other bioplastic polymers. Fibers may be used as raw materials in the production of lignocellulosic ethanol. Residue materials from ethanol production contain fibers from which ethanol has been extracted. However, only about 50-70% of the ethanol in these materials is typically extracted leaving substantial portion of ethanol that is available for further extraction. Tables 1 and 2 provide a typical content breakdown of the various materials in DDGS.

TABLE 1

Cellulosic biomass compositional analysis of DDGS.

|  | Average |
|---|---|
| Dry matter | 88.8 |
| Water extractives | 24.7 |
| Ether extractives | 11.6 |
| Crude protein | 24.9 |
| Glucan (total) | 21.2 |
| Cellulose | 16 |
| Starch | 5.2 |
| Xylan and Arabinan | 13.5 |
| Xylan | 8.2 |
| Arabinan | 5.3 |
| Ash | 4.5 |
| Total dry matter | 100.4 |

TABLE 2

Nutritional Compositional analysis of DDGS.

| Nutritional Compositional analysis | |
|---|---|
| Dry matter | 88.9 |
| Crude protein | 27.3 |
| Crude fat | 14.5 |
| Carbohydrates | 53.5 |
| Ash | 4.7 |
| Total | 100 |

It would therefore be desirable to provide a process to separate these materials in order to maximize their uses.

SUMMARY OF THE PRESENT INVENTION

In an aspect of the present invention, a multi-stage substantially continuous process for separating a source stream said source stream intermixedly containing fibers, water, protein and oil, said process being configured for separating the source stream into streams each containing predominantly one component, said source stream containing dried distillers grains with solubles, said process comprises the stages of: providing a source stream comprising dried distillers grain with solubles, said dried distillers grain stream containing water, oil, protein and fibers; separating said source stream into a second stream and a third stream, said second stream containing predominantly fibers, said third stream containing predominantly a mixture of oil, protein and water, said separating being accomplished through the treatment of the first stream with; separating a fourth stream and a fifth stream from said third stream, said fourth stream containing predominantly water and said fifth stream containing predominantly oil and protein; and separating from the fifth stream a stream containing predominantly oil and a stream comprising predominantly protein through the steps of drying, size reduction, and pressing out the oil.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention.

The main components of Raw Dried Distillers Grains with Solubles (DDGS) include water in the range of between about 70% to about 95%, but could also be higher or lower depending on the source.

It is desirable that the water content of the source DDGS stream be consistent in order for the process to be stable. Therefore, water is added as needed to ensure that the solids level in the DDGS entering the process does not exceed 30%.

The process consists of mechanical separation steps aided by polymeric additions to separate the DDGS into four streams each containing predominantly one component: fibers, water, oil and protein.

Figure 1:
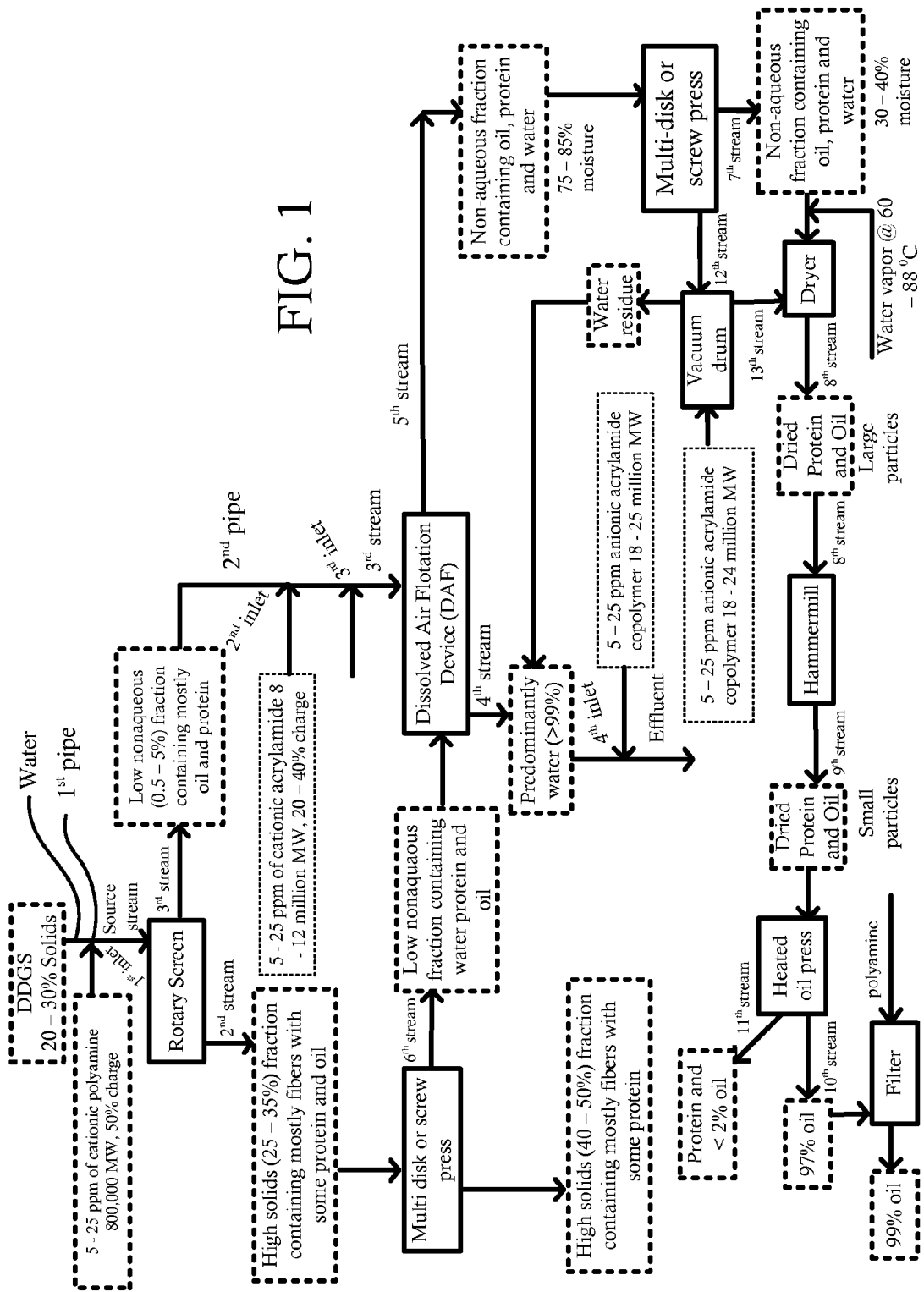
FIG. 1 is a flow chart schematic of the process according to an embodiment of the present invention.
Figure 2:
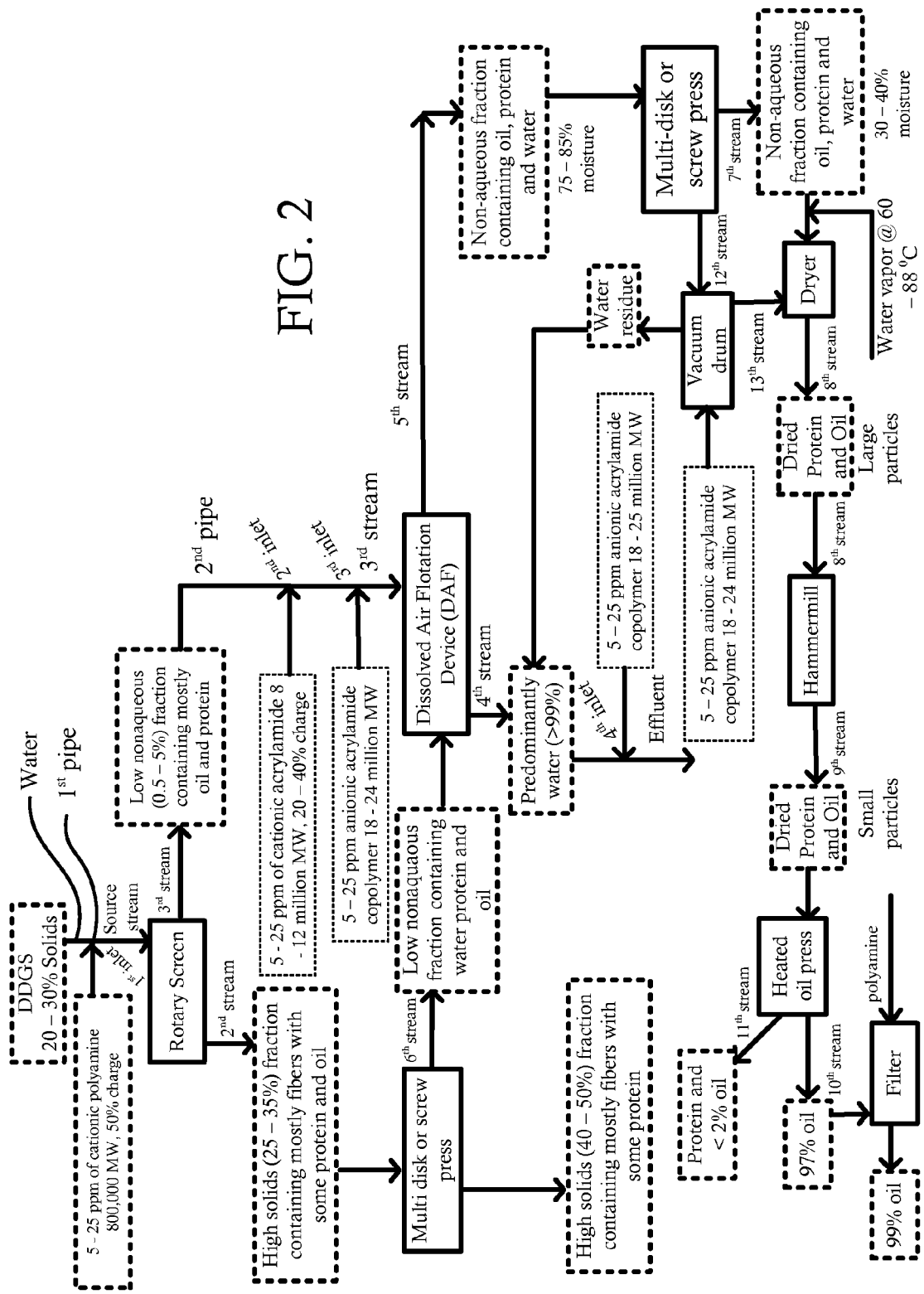
FIG. 2 is a flow chart schematic of the process according to another embodiment of the present invention.

In the first step, the DDGS source stream is introduced into a rotary screen through a 1" pipe. Between 5-25 ppm of a cationic polyamine having a 50% charge and a MW of about 800,000 are added to the pipe. This helps precipitate a stream that contains water and non-aqueous matter, predominantly fibers ranging in length from some 0.01" to as long as 0.5 inches, and having a non-aqueous content of between about 25% and about 35%. This stream, labeled as the $2^{nd}$ stream in FIGS. 1 and 2 is passed through a press that squeezes fluid from this stream and concentrates it to between about 40% to about 50% solids. The fluid removed from the $2^{nd}$ stream by the press contains water and some protein and oil. It is labeled as the $6^{th}$ stream, and is further processed to separate any oil and protein from it. The press may be a multidisc press or a screw press; however other press types also fall within the scope of this invention.

It is noted that the term "contains predominantly" refers to a content of more than 50% in the context of the present invention.

The low solids stream exiting the rotary screen contains predominantly water at between 95 percent and 99 percent, and oil and protein at between 1 to about 5 percent. It is labeled as the third stream in FIGS. 1 and 2. The third stream is sent to a Dissolved Air Floatation device (DAF) where it is separated into a fourth stream containing predominantly water at >99% and a fifth stream containing between about 75% to about 85% water and non-aqueous matter containing mostly protein and oil. Helping with the separation is polymer addition going into the pipe leading to the Dissolved Air Floatation device using the $2^{nd}$ and/or $3^{rd}$ inlets. If the pH of the third stream is lower than 5.5, between about 5 to about 25 ppm of a cationic acrylamide copolymer are added to the $2^{nd}$ inlet as shown in FIG. 1 which represents the schematic of the process for a DDGS stream having a pH<5.5. If the pH of the third stream is greater than 5.5, between about 5 to about 25 ppm of anionic acrylamide copolymer having a MW of between about 18 million to about 24 million is also added to the $3^{rd}$ inlet as shown in FIG. 2 which represent the schematic of the process for a DDGS stream having a pH>5.5.

The cationic acrylamide copolymer has a Molecular Weight of between about 8 million and about 19 million and between about 20 percent to about 40 percent charge.

The sixth stream may be combined with the fourth stream prior to entering the Dissolved Air Floatation device or combined with the effluent water in the fourth stream, depending on the oil and protein content of the sixth stream.

The $3^{rd}$ inlet is set about 15 seconds below the second inlet calculated based on the average volumetric flow rate through the pipe.

Next, the fifth stream is passed through either a multidisc press or a screw press that separates out of the fifth stream a low moisture (<30%) stream labeled as the seventh stream and a high moisture stream (>40%) labeled as the $12^{th}$ stream in FIGS. 1 and 2. The $12^{th}$ stream is passed through a vacuum drum to reduce the moisture content of the $12^{th}$ stream to between about 20 percent and about 30 percent. To aid in the water removal, about 5 to about 25 ppm of anionic acrylamide copolymer having a MW of between about 18 to about 24 million are added to the vacuum drum. The water removed from the vacuum drum is combined with the fourth stream and the combined water stream is treated with between about 5 to about 25 ppm of anionic acrylamide copolymer having a MW of between about 18 million to about 24 million in order to reduce the COD and BOD of the stream to dischargeable levels. The lower moisture stream exiting the vacuum drum is labeled as the $13^{th}$ stream.

The seventh stream is passed through a dryer where most of the moisture is removed leaving a cake of protein and oil having relatively large material chunks generally from about 0.1 inches to about 0.3 inches. This cake is labeled as the eighth stream. Also entering the dryer is the $13^{th}$ stream where it combines with the seventh stream.

The eighth stream is passed through a hammermill that reduces the particle sizes to generally less than 0.1" thereby generating a ninth stream. The ninth stream exiting the hammermill is pressed to separate out a stream that is predominantly oil ($10^{th}$ stream) from the cake and leaving the cake with a predominantly protein content ($11^{th}$ stream). The predominantly oil stream is about 97% pure. The press may be a heated oil press or another type of press suitable for this step. Water vapor in a temperature range of between 60° C. and about 88° C. may optionally be injected prior to the dryer to preheat the seventh stream and increasing moisture uniformity in the stream. The tenth stream may further be filtered and any residual protein precipitated out with the aid of between about 5 ppm to about 25 ppm of a cationic polyamine having a 50% charge and a MW of about 800,000 to bring the purity of the tenth stream to around 99%.

The following represents the important characteristics of the polymers used in the process.

Polyamines

Molecular weight between 10,000 and 1,000,000.

Liquid form with 40 to 50% concentration.

Cationic site on the main chain.

Viscosity at 50% concentration of between 40 and 20,000 centipoises.

Any polyamine having two $H_2N$ groups may be used in this application. An example may be 1,3-diaminopropane.

Cationic Acrylamide Copolymers

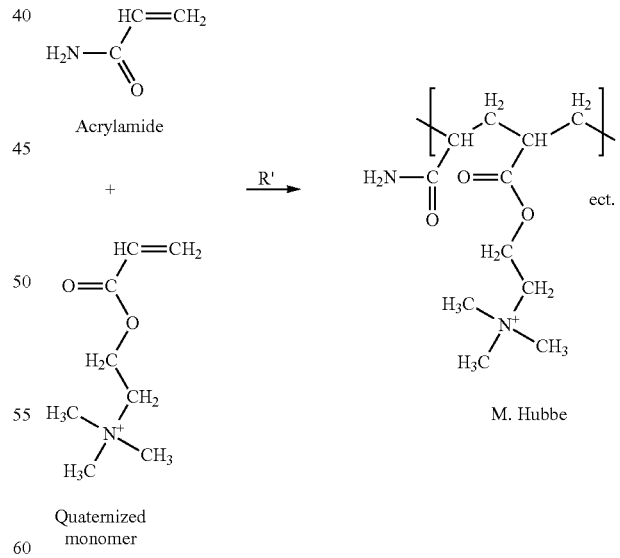

Quaternized monomer

M. Hubbe

Sodium or Potassium Anionic Acrylate Acrylamide Copolymer.

This polymer may be made from the reaction between an acrylamide monomer and an acrylic acid monomer as shown below.

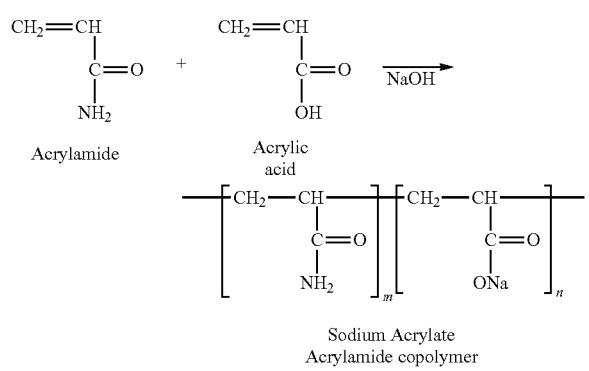

The anionicity of these copolymers can vary between 0% and 100% depending on the ratio of the monomers involved. The anionic copolymers used in the process of the present invention may have a molecular weight ranging between about 3 million to about 30 million, and a viscosity at a concentration of 5 g/l ranging from about 200 centipoises to about 2800 centipoises. The preferred pH range for making these copolymers is from 4.5 to 9. It is also noted that potassium may be substituted for the sodium as the base in the Acrylate Acrylamide copolymer.

It should be understood, of course, that the foregoing relates to exemplary embodiments of the invention and that modifications may be made without departing from the spirit and scope of the invention.

I claim:

1. A multi-stage substantially continuous process for separating a source stream said source stream intermixedly containing fibers, water, protein and oil, said process being configured for separating the source stream into streams each containing predominantly one component, said source stream containing dried distillers grains with solubles, said process comprising the stages of:
providing a source stream comprising dried distillers grain with solubles, said dried distillers grain stream containing water, oil, protein and fibers;
separating said source stream into a second stream and a third stream, said second stream having a non-aqueous portion containing predominantly fibers, said third stream having a non-aqueous portion containing predominantly a mixture of oil and protein,
separating a fourth stream and a fifth stream from said third stream, said fourth stream containing about 99 percent water and said fifth stream containing between about 15 percent to about 25 percent oil and protein,
wherein separating the fourth stream and the fifth stream from said third stream is accomplished by passing said third stream through a second chemical additive pipe having a second chemical addition inlet and a third chemical addition inlet, said second chemical additive pipe leading toward a Dissolved Air Floatation device, said third chemical addition configured to occur about 15 seconds after the second chemical addition based on an average volumetric flow rate through the pipe; adding between about 5 to about 25 ppm of a cationic acrylamide copolymer to the second chemical addition inlet; and feeding said third stream into the a Dissolved Air Floatation device wherein actions of said Dissolved Air Floatation device separate said third stream into the fourth stream and the fifth stream; and
separating from the fifth stream a stream containing predominantly oil and a stream comprising predominantly protein through the steps of drying, size reduction, and pressing out the oil.

2. The process of claim 1, wherein separating the source stream into the second stream and the third stream is accomplished by:
passing said source stream through a first chemical additive pipe having a first chemical addition inlet, said first chemical additive pipe leading toward a rotary screen;
adding between about 5 to about 25 ppm of cationic polyamine to the first stream at said first chemical addition inlet; and
separating the second stream and the third stream from said source stream in the rotary screen.

3. The process of claim 1 wherein separating the fifth stream a stream containing predominantly oil and a stream comprising predominantly protein is accomplished by the steps of:
removing water from the fifth stream to achieve between about 90 percent and about 95% solids, said water removal being accomplished by a pressing step, a vacuuming step and a drying step, said water removal step generating an eighth stream, said eighth stream constituting of a dried cake containing predominantly oil and protein having a particles ranging in size between about 0.2 inches to about 0.5 inches;
reducing the particle size of the eighth stream by passing said eighth stream through a hammermill to generate a ninth stream, said ninth stream constituting of a dried cake containing predominantly oil and protein having particles ranging in size from between about 0.05 inches to about 0.2 inches; and
separating the ninth stream into a tenth stream containing predominantly oil and an eleventh stream containing predominantly protein, said separating being accomplished by passing the ninth stream through a heated oil press.

4. The process of claim 3 further comprising passing the tenth stream through a filter, while adding between about 5 to about 25 ppm of cationic polyamine to said filter based on the average volumetric flow rate through the pipe, said polyamine addition resulting in precipitating any protein residual from said tenth stream.

5. The process of claim 3 further comprising pressing the fifth stream, said pressing being accomplished in either a multidisc press or a screw press, wherein pressing separates the fifth stream into a seventh stream having a water content between about 30 percent and about 40 percent and a twelfth stream containing a water content of above 40 percent, said twelfth stream being passed through a vacuum drum, said vacuum drum removing a water residue stream, said water residue stream being combined with the fourth stream.

6. The process of claim 5, further comprising adding to the vacuum drum between about 5 to about 25 ppm of anionic acrylamide copolymer having a MW of between about 18 million to about 24 million.

7. The process of claim 3 wherein drying constitutes passing the seventh stream through a dryer wherein water vapor in a temperature range of between about 60° C. and about 88° C. is injected prior to drying.

8. The process of claim 1, further comprising passing said second stream through a press to generate a sixth stream, said sixth stream containing predominantly water, and combining the sixth stream with the third stream prior to entering the Dissolved Air Floatation device.

9. The process of claim 1 further comprising treating the fourth stream with between about 5 to about 25 ppm of anionic acrylamide copolymer to reduce COD and BOD levels of said fourth stream.

10. The process of claim 1 further comprising adding between about 5 to about 25 ppm of an anionic acrylamide copolymer to said third chemical addition inlet if the pH of the third stream is greater than 5.5.

11. The process of claim 1, wherein a charge of the cationic acrylamide copolymer is in a range of between about 20 percent and 40 percent.

* * * * *